United States Patent [19]

Williams et al.

[11] Patent Number: 4,941,475
[45] Date of Patent: Jul. 17, 1990

[54] THERMODILUTION BY HEAT EXCHANGE

[75] Inventors: Wilbur R. Williams; Gene A. Bornzin, both of Camarillo; John S. Thompson, Oxnard, all of Calif.

[73] Assignee: Spectramed, Inc., Oxnard, Calif.

[21] Appl. No.: 394,252

[22] Filed: Aug. 7, 1989

Related U.S. Application Data

[63] Continuation of Ser. No. 239,128, Aug. 30, 1988, abandoned.

[51] Int. Cl.$^5$ .............................................. A61B 5/028
[52] U.S. Cl. .................................. 128/692; 128/713; 128/736
[58] Field of Search .................. 128/691–692, 128/713, 736, 399–400; 73/204.11–204.13

[56] References Cited

U.S. PATENT DOCUMENTS

| | | | |
|---|---|---|---|
| 3,915,155 | 10/1975 | Jacobson et al. | 128/692 |
| 4,502,488 | 3/1985 | Degironimo et al. | 128/692 |
| 4,508,123 | 4/1985 | Wyatt et al. | 128/692 |
| 4,685,470 | 8/1987 | Sekii et al. | 128/692 |
| 4,730,623 | 3/1988 | Lee | 128/692 |
| 4,796,640 | 1/1989 | Webler | 128/692 X |
| 4,819,655 | 4/1989 | Webler | 128/713 |

FOREIGN PATENT DOCUMENTS 0235811  9/1987  European Pat. Off. ............. 128/692

Primary Examiner—Angela D. Sykes
Attorney, Agent, or Firm—Roger M. Rathbun; Larry R. Cassett

[57] ABSTRACT

Heat is removed from the blood flow by heat exchange rather than cold-liquid injection; resulting temperature changes are monitored. Flow rate is found from monitored temperature and known parameters related to the amount of heat removed. Preferably heat is removed by pumping cold liquid into a sealed balloon or sheath along a catheter, which is in the blood stream. The balloon acts as a heat exchanger; its design optimizes that function. Temperature can be monitored by a thermistor or other sensor closer to the tip of the same catheter. Alternatively it appears possible to use blood-temperature measurements taken just outside the balloon, or even within the balloon, if the system is calibrated to account for the relation between the blood flow rate and the heat lost from balloon to blood. Heat removal can be either quasi steady-state or cyclical: that is, either heat is removed semicontinuously by a low-temperature-differential exposure and resulting steady-state temperatures observed semicontinuously; or heat is removed periodically in brief high-differential exposures, and temperature changes tracked in defined time periods during or after each exposure. In the latter case, a patient's heat balance can be maintained by alternately adding heat in protracted low-differential exposures.

13 Claims, 5 Drawing Sheets

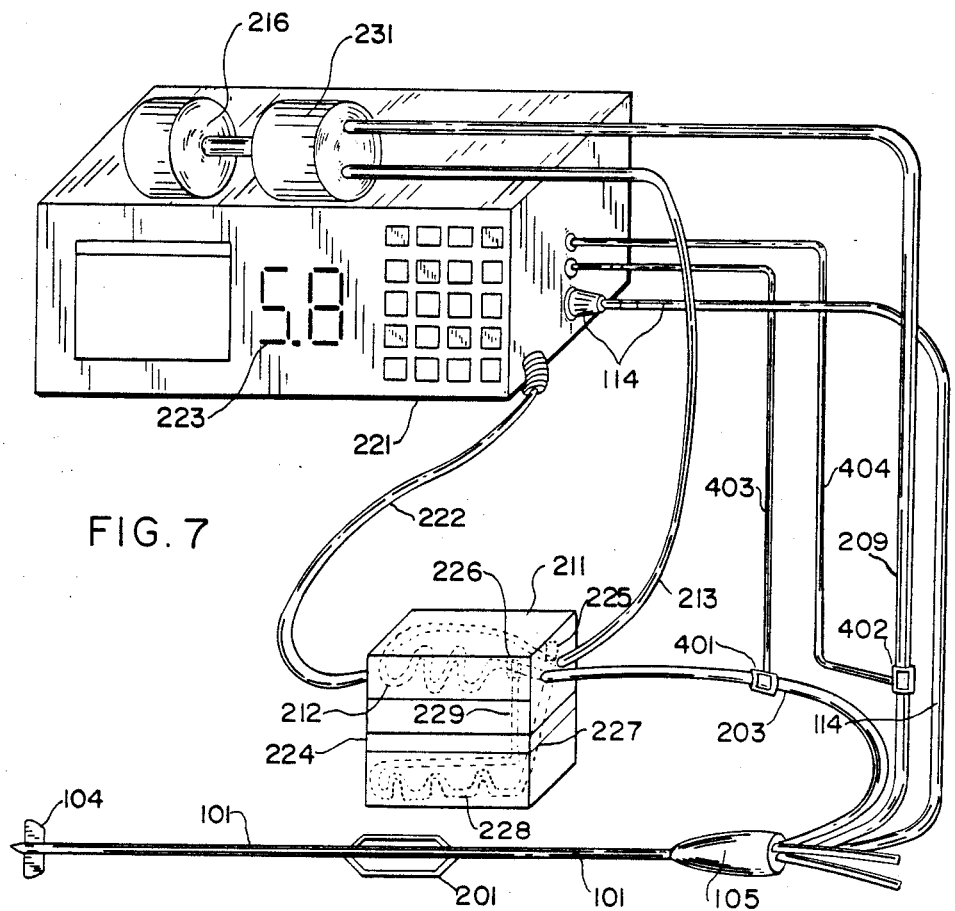

THERMODILUTION BY HEAT EXCHANGE

This application is a continuation of application Ser. No. 239,128, filed Aug. 30, 1988, now abandoned.

BACKGROUND

1. Field of the Invention

This invention relates generally to medical procedures and appliances used in diagnosis or therapy; and more particularly to procedures and apparatus for determining flow rate of blood in a living body.

2. Prior Art

At present, cardiac output is most often measured by the thermodilution method. This process requires starting a right-heart catheter in a vein (jugular or subclavian).

The catheter tip is advanced to the vena cava through the right atrium and ventricle, and finally placed in the pulmonary artery. Generally this process is facilitated by floating the catheter tip into position using a balloon, approximately one-and-a-third centimeter in diameter, attached to the catheter tip.

The catheter has a lumen running to the right atrium region, with a port in that region. This port allows rapid infusion of a bolus of cold liquid, ordinarily three to ten cubic centimeters of room-temperature or iced saline solution (or five percent dextrose in water), which mixes with the blood flowing through the right ventricle. Mixed blood and bolus then flow out the pulmonary artery.

The temperature of the resulting mixture of blood and added liquid leaving the ventricle is depressed—relative to the initial temperature of the blood alone—by the cold bolus. Temperature in the pulmonary artery is then measured with a thermistor carried on the catheter about three and a half centimeters from the catheter tip.

Cardiac output is calculated from the temperature drop in the pulmonary artery following cold-bolus injection. The duration of the temperature transient ranges from six to about thirty seconds, depending on the patient's cardiac output. The area under the temperature-transient curve is inversely proportional to cardiac output; therefore to calculate the flow it is necessary to divide an empirical constant by the area under the curve.

Injected dye is sometimes used in place of an injected cold bolus. When dye is used, arterial blood is withdrawn slowly. The concentration of dye in the withdrawn blood is then measured as a function of time and used to compute cardiac output.

It has also been proposed to perform a modified type of thermodilution by adding heat to the blood flow and measuring the resultant temperature rise. Heat can be added through operation of a resistive heater on a catheter, without liquid infusion, as suggested by Philip et al. in "Continuous Thermal Measurement of Cardiac Output," *IEEE Transactions on Biomedical Engineering*, volume BME-31 No. 5, May 1984, at 393–400.

Other techniques sometimes used are known as the Fick method and the ultrasound method. In the Fick technique, three measurements are necessary: measurement of arterial and mixed-venous blood-oxygen content, and measurement of the rate of oxygen consumption.

The Doppler ultrasound technique measures cardiac output noninvasively. A Doppler probe operating at about five megahertz is placed in the suprasternal notch (the indentation beneath the "Adam's apple") and directed at the ascending aorta. The velocity of the blood thus measured is multiplied by the estimated cross-sectional area of the aorta lumen. The result is an estimation of flow; the estimate can be averaged to determine cardiac output.

All these methods are subject to important drawbacks. Thermodilution and its dye variations typically require the clinician to inject three to ten cubic centimeters of liquid. This is inconvenient, intermittent, and can result in excessive fluid infusion into the patient.

Excessive infusion in turn can increase risk of congestive heart failure or kidney failure in certain patients. Because of this problem, frequent automated injection of fluid is precluded—even though the physician would like to know cardiac output on a minute-to-minute basis. In addition the injection of fluid increases risk of infection.

In addition, the dye variant poses yet another problem. Some patients seem to have exhibited hypersensitive reactions to the material used as dye.

The Philip heating technique poses a problem of potential injury to the patient. As explained in the paper by Philip et al., investigators have yet to establish the maximum permissible temperature rise in any significant fraction of a patient's blood volume; but preliminarily that permissible rise appears to be rather narrowly constrained. Philip and his coauthors predict "feasibility in most mechanically ventilated patients, but difficulty in spontaneously ventilating, more active patients"—and then go on to conclude that "technical difficulties of developing a clinically practical system are formidable . . ."

The Fick method requires the patient to be in a steady state in which cardiac output does not change significantly on a minute-to-minute basis. This constraint is not a realistic one for surgical cases of practical importance. In addition, the Fick method not only requires precise measurement of arterial and venous blood oxygen, using blood samples, but also requires very expensive or inconvenient instrumentation for measurement of oxygen consumption.

The method is thus cumbersome and expensive. Hillis et al. present a fuller discussion in "Analysis of Factors Affecting the Variability of Fick Versus Indicator Dilution Measurements of Cardiac Output," *The American Journal of Cardiology*, volume 56, at 764–68 (Nov. 1, 1985).

The Doppler method is sensitive to orientation of the probe. It also requires an estimate of the cross-section of the aorta lumen, using either M-mode ultrasound or a statistically based empirical table. In either case the area estimations are troublesome and inaccurate. More details appear in, e.g., "Non-Invasive Ultrasonic Cardiac Output Measurement in Intensive Care Unit," Levy et al., *Ultrasound in Medicine & Biology*, volume 11 number 6, at 841–49 (1985).

In summary, the prior art leaves much to be desired in the convenient and continuous measurement of cardiac output.

SUMMARY OF THE DISCLOSURE

Our invention provides both apparatus and procedures for determining flow rate of blood along a flow path in a living body. The process includes the step of removing heat from the blood flowing through the body, by heat exchange at a position along the flow path, without liquid injection into the blood.

It also includes the step of monitoring temperature; and the step of determining flow rate from the monitored temperature and known parameters related to the amount of heat removed.

The foregoing may be a definition of the process of our invention in its broadest or most general form. At the outset one can appreciate from this definition that our method avoids all the disadvantages of fluid overloading and cumulative temperature rise in prior methods, for our method involves neither liquid injection nor a net addition of heat to the body. Similarly our method circumvents the disadvantages of the Fick and ultrasound methods, since our invention entails neither chemical determinations nor cross-section estimates.

We prefer, however, to incorporate additional steps or constraints in practice of this novel method. These added features optimize even further the enjoyment of its potential benefits.

In particular we prefer that the heat exchange be between the blood and a cooler medium. We prefer to effect the heat exchange by exposing the blood to a heat-exchange device containing the medium, but not to the medium itself. The medium advantageously is placed in and removed from the heat-exchange device by pumping through a fluid circuit from outside the body.

We prefer that the temperature measured be that of the blood, and preferably at another position—usually one that is downstream from the heat-exchange position—along the flow path. In this connection it is to be appreciated that in principle, by virtue of heat-flow relationships, the temperature measured may instead be that of the blood at or near the heat-exchange position, or even that of the heat-exchange device or heat-exchange medium itself.

For best measurement accuracy when the temperature used is downstream from the heat-exchange position, we prefer to also measure the temperature of the fluid within the heat exchanger—or of the same fluid at points outside the body as the fluid enters and leaves the catheter Such auxiliary measurements permit more accurate calculation of heat removed from the blood, and therefore of cardiac output. The improved calculation is obtained by using the additional information to correct for spurious heat leakage into the exchange medium along portions of the fluid circuit other than the intended heat-exchange site (i.e., other than the balloon).

We also prefer to repeat periodically the sequence of removing, monitoring and determining steps. In this case we further prefer to also add heat to the blood flow: the heat-addition step is performed between each pair of successive periodic repetitions.

In this way it is possible to at least roughly preserve a balance of heat flow to and from the body. Furthermore the temperature modulation is increased—in fact doubled, on the basis of area under the temperature-vs.-time curve.

Generally we prefer to remove heat for a very short time, using a relatively high temperature differential (which is to say, a relatively high rate of heat removal). These conditions optimize measurement signal-to-noise ratio. When heat is also being added, we prefer that heat be removed for a much shorter time than heat is added, and that the rate of heat removal be much greater than the rate of heat addition.

In an alternative procedure, we prefer to perform the removing step at a generally constant rate of heat removal so that the temperature monitored in the monitoring step reaches a steady state, or steady value, that is characteristic of the flow rate. Thus this value, although we describe it as "steady," tends to vary with fluctuations in the flow rate.

When this alternative procedure is used, the monitoring step continues while—and after—the monitored temperature first reaches a steady state. The determining step then proceeds to determine the flow rate, particularly including any fluctuations in it, from the rate of heat removal and the monitored temperature.

In using this alternative, each temperature value used for cardiac-output calculations—or in any event each calculated value of cardiac output—should preferably represent an average over a time period sufficient to significantly reduce imprecision due to rapid fluctuations in temperature, or "thermal noise." If desired, this multiplicity of averages may be discrete values; if preferred, however, the values found may be a substantially continuous output signal that results from passing the temperature input signal or resultant cardiac-output signal through a transfer function with a suitable time constant.

For maximum precision and accuracy in the steady-state method, temperature monitoring preferably is interrupted from time to time to reestablish a zero-heat-transfer baseline level. (Hence even this "steady state" method is advantageously periodic or at least repetitive in a sense.) When such a baseline reevaluation is considered necessary, a modified area-under-the-curve calculation may be advantageously employed.

Other algorithms may be developed for use to avoid collecting baseline data as such, or in situations when it is appropriate to assume adequate baseline stability. Some preferred data-handling procedures will be detailed in a later section of this document.

It will be understood, however, that a very great variety of data-processing approaches are available for use within the scope of our invention. We cannot discuss or even know all of such approaches at the time of this writing.

We turn now from processes to apparatus of our invention. The invention provides a cardiovascular diagnostic system, for use with a heat-exchange medium in determining flow rate of blood along a flow path in a living body.

The system includes a catheter which has a distal end (that is, distal with respect to medical personnel) for insertion into the blood flow path in the body. A heat-exchange device is positioned along or is part of the catheter.

In addition the system includes some means for conveying the medium along the catheter, to and from the heat-exchange device, relative to a position outside the body. For generality in expression of our invention, we shall refer to these means as the "conveying means."

The conveying means and the heat-exchange device are adapted to permit withdrawal of heat from the blood into the heat-exchange medium, but to prevent flow of the medium itself into the blood.

The system also has some means for monitoring temperature. Again for generality of expression, we shall call these the "monitoring means." The monitoring means are disposed along the catheter.

The preceding may be a definition of the apparatus of our invention in its broadest or most general form. We prefer, however, to incorporate additional elements or features, to even further optimize its performance and usefulness.

In particular we prefer that the heat-exchange medium be substantially saturated saline or dextrose in water, and that the cooling means cool the medium to near zero Celsius, or several degrees below. We find that cooling the medium to about ten degrees below zero Celsius is particularly satisfactory.

We prefer that the conveying means include a pair of opposing lumens within the catheter. In addition we prefer that the system also include means for minimizing heat transfer between the pair of lumens—again for generality, the "heat-transfer minimizing means."

These latter means preferably include insulating structure interposed between the lumens. Advantageously, where permissible, the insulating structure includes a barrier lumen which during use is filled with gas at a pressure that is significantly lower than atmospheric pressure.

The primary purpose of any of these forms of heat-transfer minimizing means is to maximize the temperature differential between the blood just outside the exchange device and the medium within. As mentioned earlier, signal-to-noise ratio and therefore measurement precision and accuracy are best when this temperature differential is very large.

It is therefore desirable to maintain as much as possible of the total available temperature differential—namely, the difference between the temperatures of the blood and an external heat sink—during movement of the heat-exchange medium from the external heat sink to the exchange device inside the body. This temperature differential is degraded to the extent that warmer liquid leaving the heat-exchange device in one lumen can transfer heat to the cooler liquid approaching the exchange device in another lumen.

We also prefer that the heat-exchange device include or take the form of a balloon positioned along the exterior of the catheter. By the term "balloon" we intend to encompass not only a outward-bulging structure characteristic of ordinary balloons, but also a structure that closely adheres to the underlying catheter segment—or may even have the same external diameter as adjacent catheter segments—and that might accordingly be termed a "sheath."

Either type of balloon preferably has a thin wall of a plastic whose thermal conductivity is high—such as, for example, a plastic that has a high loading of silica. More specifically we prefer to use either irradiated polyethylene or the plastic available commercially under the name Mylar. The balloon preferably has wall thickness on the order of five-hundredths to one-tenth millimeter, diameter very roughly three-tenths to two centimeters, and length very roughly six to ten centimeters.

In some cases it is preferable to use only a single lumen for the conveying means, and to pump the heat-exchange medium in and out through the single lumen—inflating and collapsing the balloon in the process. In these cases it is preferable that the lumen have a total volume, for the medium, which is much smaller than that of the heat-exchange device.

This relationship will minimize the fraction of liquid in the heat-exchange device that only moves back and forth in the catheter, never reaching the external heat sink. Once again, the result is to minimize dilution of the thermal signal and thereby maximize temperature differential, and accordingly optimize signal-to-noise ratio, precision and accuracy.

All of the foregoing operational principles and advantages of the present invention will be more fully appreciated upon consideration of the following detailed description, with reference to the appended drawings, of which:

BRIEF DESCRIPTION OF THE DRAWINGS

FIG. 7 is a system schematic representation, similar to that of FIG. 3, but showing a system that employs the FIG. 6 catheter body.

FIG. 8 is a cross-section of an another embodiment, namely a catheter in which two lumens with thin outboard walls are used instead of a balloon.

DETAILED DESCRIPTION OF THE PREFERRED EMBODIMENTS

Figure 1:
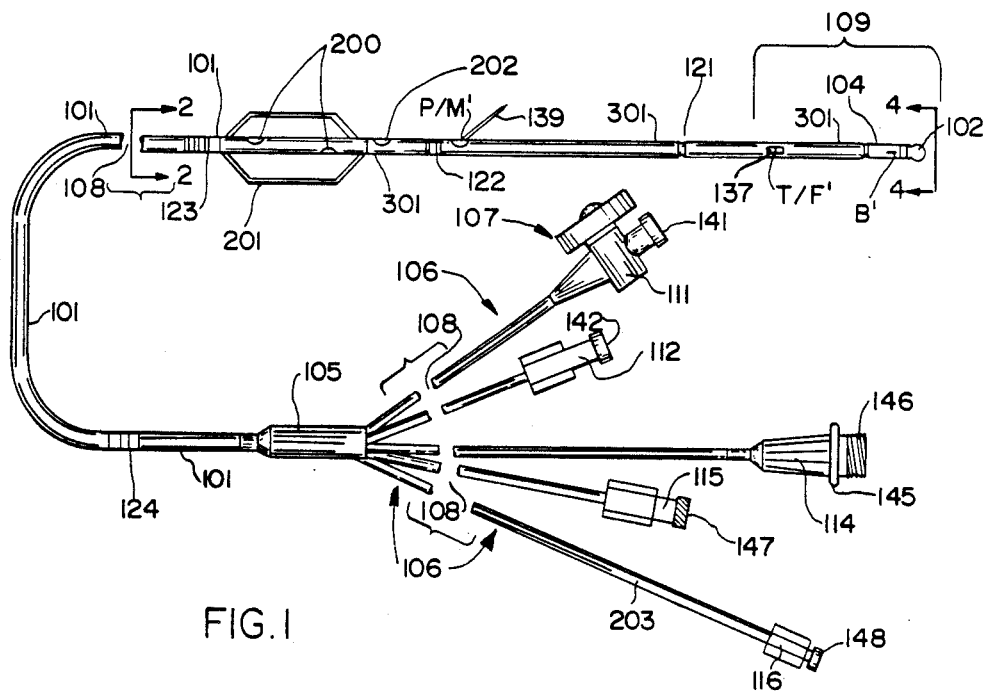
FIG. 1 is a somewhat schematic view, which may be considered either a plan or an elevation, of a catheter system in accordance with a preferred embodiment of our invention. Because of the considerable length of the instrument, it is drawn partially broken away.

As shown in FIGS. 1 through 4, one preferred embodiment of our invention makes use of a five-lumen catheter 101/301. It is a right-heart catheter with a balloon 201 placed over a pair ports 200. The catheter diameter, except for the balloon 201, is preferably 7.5 French or less.

The ports 200 are both connected to a single, common lumen P that runs down the catheter to an extension tube 203. The balloon 201 can be inflated with cold fluid while the balloon is in place in a patient's body with the balloon in the right atrium.

Suitably cold liquid such as ice-cold saline is preferably prepared by refrigeration in the Peltier cooler 211. The liquid-carrying lumen 212 within the cooler 211 is pressurized through a liquid-filled tubulation 213 by a syringe 214, driving the cold liquid through the extension line 203 (and a mating tubulation 203' at the cooler 211), the catheter proximal segments 101, and the ports 200 into the balloon 201.

Although we prefer to make the heat-exchange balloon 201 of inelastic material such as irradiated polyethylene, elastic materials such as latex or silicone can also be used. We prefer Peltier-effect coolers for their versatility and convenience, but our invention is compatible with compressor-type refrigerators or even ice.

Preferably the plunger 215 of the syringe 214 is actuated by a driver motor 216 under control of electronic circuitry (not shown) in a control-and-readout unit 221. The balloon 201, when filled with cold fluid from the cooler 211, then cools the blood in the atrium and the right vena cava.

An electrical umbilicus 222 provides timed and regulated power from the control-and-readout unit 221 to the cooler 211. The motor or syringe, or both, are mounted upon or within the unit 221 as shown, or if preferred may be associated with the cooler 211—in which case the umbilicus 222 also carries controlled power for the motor.

Blood-temperature depression in the pulmonary artery is measured with a thermistor located along the catheter at T/F'. Excitation current and temperature signals are transmitted between the thermistor T and the control-and-readout unit 221 through an electrical extension and connector 114.

As in the earlier thermodilution systems, the area under the temperature-time curve is inversely proportional to the cardiac output. Necessary calculations are performed in the control-and-readout unit 221 in a generally conventional way—except that the time scale, signal levels and proportionality factor are different—to provide a suitable readout 223 of cardiac output.

Fluid can be withdrawn from the balloon 201, recooled and then reinfused into the balloon. Upon reinfusion, the cardiac output can be measured again, using the same method.

Figure 5A:
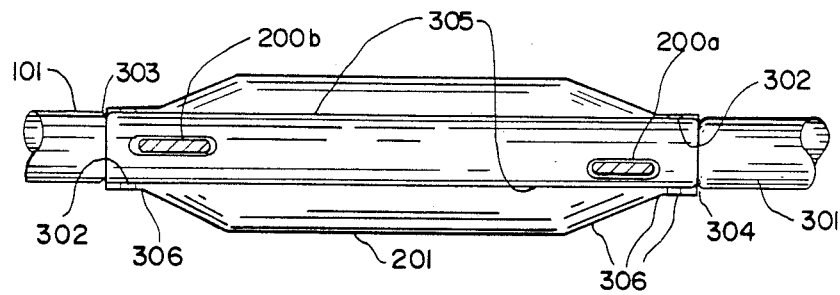
FIGS. 5a and 5b are enlarged longitudinal sections showing the details of form and attachment of, respectively, two forms of heat-exchange balloon for use in the same embodiment.

As shown in FIG. 5a, the catheter tubing 101/301 at both ends of the balloon is necked down slightly in the region 305 where the balloon is fixed. This helps accommodate the collapsed balloon as it is inserted through a conventional catheter introducer into a patient's body. The balloon 201 is necked down at both its ends 306 so that its inside diameter approximates the outside diameter of the necked-down catheter tubing segment 305. Cyanoacrylate adhesive 302 can be used to bond the balloon 201 to the catheter tubing 202.

A balloon thickness of one-twentieth to one-tenth millimeter is preferable for high flexibility and rapid heat transfer. It is also preferable because it only negligibly adds to the outer diameter of the catheter in the balloon region.

The balloon need not be inflated so fully that it becomes a rigid cylinder, but rather may be inflated only partially. Partial inflation permits the balloon to assume a configuration closer to a slab than a cylinder, with correspondingly better heat-transfer characteristics.

In addition, an underinflated balloon will conform better to the shape of the blood vessels and cardiac chambers through which the balloon passes and in which it eventually is located for measurements. This conformance may be an advantage for maintaining blood flow and reducing the likelihood of trauma to the blood vessel.

If desired a single port, e.g. 200a, can be used to both fill and empty the balloon 201 through a catheter lumen. If preferred, however, a second port 200b may be used in conjunction with the first port 200a to establish continuous flow through the balloon.

As to this second possibility, in other words, the distal port 200a can provide an input path for fluid while the proximal port 200b provides an outflow path. Some such arrangement is required for a circulating-exchange-medium system.

For the periodically repeating embodiments of our invention (that is, particularly those using very brief, high-differential heat-exchange "spikes" as the thermal excitation for the monitoring system), circulation may be regarded as optional. We believe that adequate thermal signals can be developed using a single lumen P (FIG. 2) for both filling and emptying the balloon 201; and we prefer such a system for the correspondingly reduced overall diameter of its catheter 101/301.

For quasi steady-state operation, however, maintaining the balloon at substantially constant temperature is required or at least preferred. This condition is most readily satisfied by using a circulating system to continuously replenish cold liquid in the balloon.

Figure 5B:
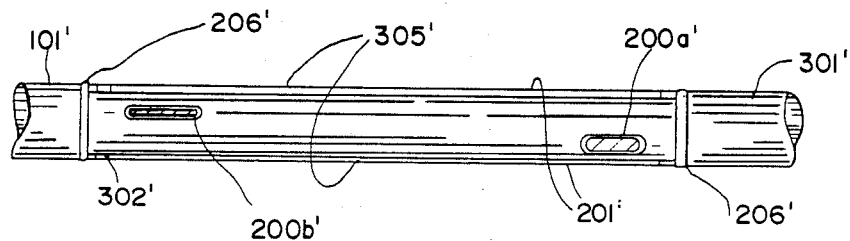

FIG. 5b shows an alternative heat-exchanger balloon 201' configured as a sheath. This balloon 201' has a very low profile, which minimizes the overall increase in catheter diameter caused by adding the balloon to the catheter body. This geometry is advantageous because it permits advancement of the catheter into the patient's body easily through an eight-French or smaller introducer.

A balloon 201' of this nature is particularly well suited for steady-state measurements, since a constant flow of cold saline through the balloon will maintain a high differential of temperature and thus a high rate of heat removal from the blood—even though the balloon is small. Epoxy or urethane adhesive 206' may be added at the tubing-to-balloon junctions (101 and 301 to 201) in both configurations, FIGS. 5a and 5b, but for clarity of the illustrations the adhesive 206' is drawn in FIG. 5b only.

In still other embodiments the tubing itself is used as a heat exchanger. In this configuration, one lumen brings chilled fluid inward through the catheter, and a crossover passageway allows fluid to flow to a second lumen.

The second lumen returns the fluid outward along the catheter and eventually out of the catheter. A steady flow of chilled fluid in such a system can carry enough heat out of the bloodstream for measurement of cardiac output.

One or both of the exchange-medium-carrying lumens may be formed with especially thin walls in the segment of the catheter that serves as a heat exchanger. This arrangement is discussed below in relation to FIG. 8.

To provide a clear idea of the context in which the invention is used, we shall present some other details of the preferred system illustrated in FIGS. 1 through 5a or 5b.

It is to be understood that many of these additional details are merely exemplary, for the catheter system may be satisfactorily completed in any of myriad ways. The selection of features and characteristics depends upon the functions to be performed and the techniques preferred.

Fixed at the proximal end of the catheter 101 are a manifold connector 105 and five individual single-lumen tubes 106. These individual tubes respectively communicate at their distal ends with the five lumens T/F, P, B, D and P/M of the catheter 101/301—through the manifold connector 105—and at their proximal ends with five termination devices 107.

Likewise fixed at the distal end of the distal catheter segment 301 are a molded tip 102 and a second annular balloon 104. This balloon 104, as will be seen, is entirely different from the balloon 201 already discussed and is provided for different purposes—usually to help float the catheter tip 102 along the bloodstream, through the heart and into the pulmonary artery.

Figure 4:
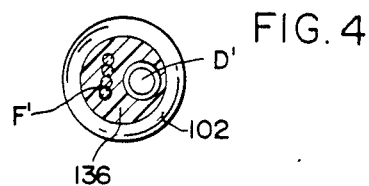
FIG. 4 is an end elevation of the catheter in the same embodiment, taken along the line 4—4 in FIG. 1 at the distal end of the catheter.

In the tip 102 is the polished distal end F' (FIG. 4) of a bundle of optical fibers F (FIG. 2), that is drawn through the lumen T/F in the catheter 101/301. Also in the tip 102 is a port or aperture D' (FIG. 4).

This distal aperture D' effectively constitutes the distal end of one of the lumens D (FIG. 2) in the catheter distal segment 301. The remaining space in the orifice of the tip is occupied with epoxy or like inert potting material 136.

As is well known in the cardiovascular field, a catheter of this general sort is inserted through the patient's vena cava into the right atrium and ventricle, with the tip 102 and its distal aperture D' extending onward into the patient's pulmonary artery. The tip 102 generally is held in that artery for pressure measurements.

The balloon 104 is formed as a short length of latex tubing, positioned over a necked-down end section of the catheter distal portions 301. The distal end of the balloon tubing 104 is doubled under and is held by adhesive to the neck portion of the tip 102.

The proximal end of the balloon tubing 104 is held by adhesive to the proximal end of the necked-down end section, and a tapered annular space just proximal to the balloon is filled with epoxy or like cement. A very small balloon-inflation aperture B' is defined in the necked-down end section of the distal catheter portion 301, communicating with the dedicated balloon lumen B (FIG. 2).

Figure 2:
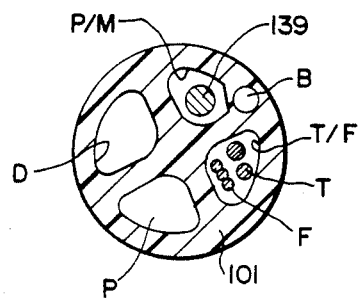
FIG. 2 is a cross-section of a preferred form of the FIG. 1 catheter body, taken along the line 2—2 of FIG. 1. This form of the catheter body has five lumens.
Figure 3:
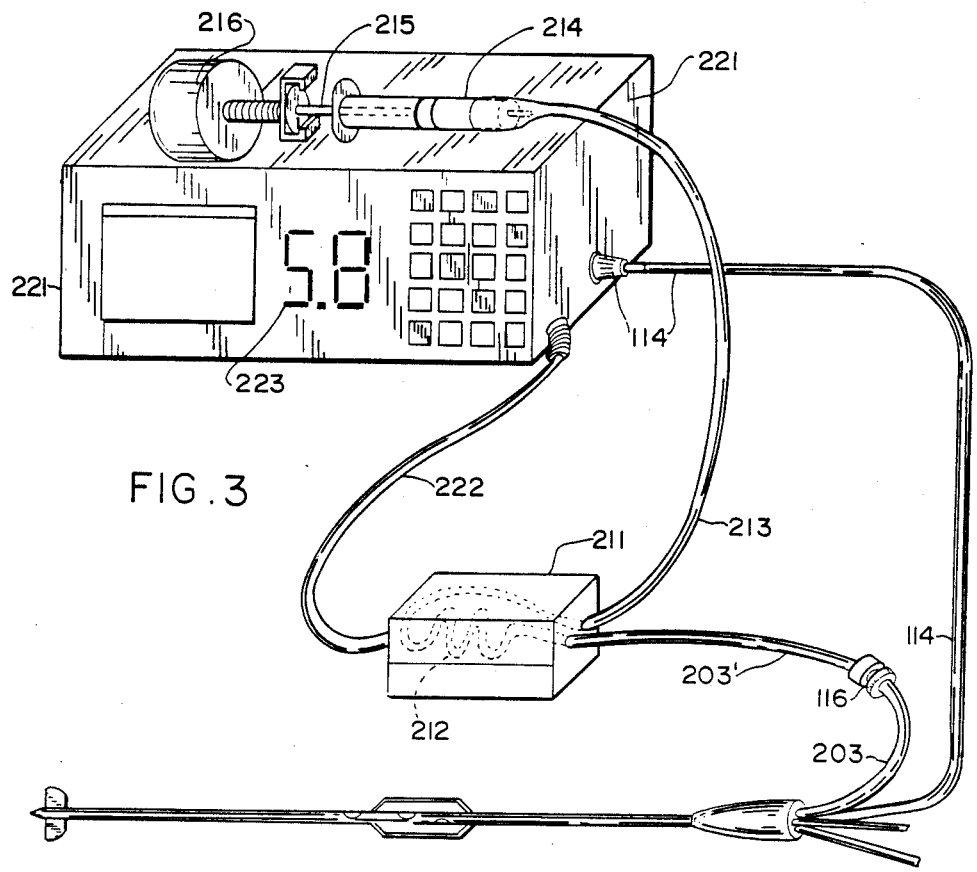
FIG. 3 is a somewhat schematic perspective representation of a cardiovascular diagnostic system employing the FIG. 1 catheter.

Three or four centimeters proximal to the tip 102 an aperture T/F' (FIG. 1) is formed in the catheter wall, communicating with the lumen T/F (FIG. 2). This aperture is occupied principally by a thermistor bead T' (FIG. 3), functionally connected at the distal end of the thermistor leads T (FIG. 2). The remainder of the aperture T/F' is filled with urethane or like potting compound 137.

In use, the balloon 104 and thermistor T' are generally passed with the tip 102 into the patient's pulmonary artery. Temperature information developed with this embodiment of our system thus may relate to the blood in that artery.

As previously mentioned, however, the extraction of heat from the blood into the heat-exchange medium—i.e., the lowering of blood temperature—can in principle be observed immediately outside the balloon. Furthermore, lowering of blood temperature has a counterpart in raising of the exchange-medium temperature.

These phenomena may possibly offer another group of monitoring locations. All these temperature changes are closely related to each other, and therefore to the blood flow rate—but with different sensitivities (which must be taken into consideration in selecting a monitoring location) to the flow rate, heart rate, fluctuations in body temperature, and other conditions.

As indicated roughly in the drawing, the thermistor leads T share the lumen T/F with the optic fibers F. This arrangement is described and explained in U.S. Pat. No. 4,718,423 to Willis et al.

Another lumen-sharing scheme that is particularly advantageous for use as part of our present invention and not disclosed in that patent is to pass the heat-exchange medium through the same lumen T/F as the thermistor leads and optic fibers—or, if the optic fibers are not in use, then through the same lumen as the thermistor leads. This system frees the lumen P for use with, e.g., an optional pacing-and-medication port 202 as described later in this document.

Eighteen to twenty centimeters proximal to the tip 102, another aperture P/M' is formed in the wall of the catheter 301, this one in communication with the lumen P/M. This lumen P/M and aperture P/M' can be left unobstructed, for measurement of pressure in the right ventricle through a fluid column in the lumen; or when desired can be used for heart pacing, as described below.

Within the lumen P/M and extending outward from the catheter 301 through the aperture P/M' is a coaxial wire 139. In use, this wire is typically positioned within the patient's right ventricle, and lies against the myocardium or heart muscle.

Near the tip of the portion of the wire that extends out through the aperture P/M', the central conductor of this wire 139 is exposed so that the outer and inner conductors form an electrode pair for application of pacing voltage pulses to the myocardium. Unused clearance space within the lumen P/M and its aperture P/M' can be used for drip administration of medication.

Such medication may include, for example, dilute heparin solution-or other anticoagulant. An anticoagulant may be important to help maintain the lumen free of clots, so that the pacing wire can be readily repositioned if required to maintain pacing.

Just distal from the pacing-and-medication aperture P/M', a very short length of stainless-steel spring wire (not shown) is inserted into the lumen P/M. This wire serves to plug the unused, distal portion of this lumen, and also to form a radiopaque marker that can be helpful in positioning the catheter with the aperture P/M' in the patient's right ventricle for proper pacing.

Extending from approximately twenty-four to approximately twenty-eight centimeters proximal to the tip 02 of the catheter 101/301, is the previously discussed heat-exchange balloon 201, communicating with the lumen P through the ports 200 (or, in FIGS. 5a and 5b, ports 200a and 200b, or 200a' and 200b'). In use these features are typically positioned within the patient's right atrium, and are used for withdrawal of substantially known quantities of heat in our heat-exchange process for cardiac output (flow rate) measurement.

If desired an optional additional aperture 202, with a communicating lumen, extension tube and fitting (none of the latter three items being shown) can also be provided for use in withdrawing or infusing liquids, or in measuring pressures near the right atrium. Such an additional aperture may be placed advantageously about thirty-one centimeters from the catheter tip.

The necessary internal conduit for such an additional aperture 202 can be provided by using a six-lumen catheter extrusion. Alternatively, if preferred, the needed conduit can be obtained in a five-lumen device by eliminating the ventricular port P/M', or by sharing lumens as noted above.

Just distal from the more distal heat-exchange aperture 200a (or 200a'), a very short rod (not shown) of solid polyvinyl chloride or the like is inserted into the corresponding lumen P. This short plastic rod is provided to block off the unused, distal portion of this lumen.

To aid in determining how much of the catheter length has been inserted into the patient's body during the initial phases of the catheterization process, markers are advantageously imprinted along the outside of the catheter at suitable intervals. For example, indicium 121 may be placed at ten centimeters from the tip 102, indicium 122 at twenty centimeters, and indicium 123 at thirty centimeters.

Each of these indicia may be a simple narrow band or group of narrow bands, each band representing a cumulative ten centimeters. More than four bands being hard to count quickly, however, it is advantageous to use a single broader band for the fifty-centimeter indicium, and then a broad band next to a narrow band to represent fifty plus ten or sixty centimeters, etc. Thus the one-hundred centimeter indicium 124 appears as a pair of broad bands.

The individual termination devices 107 at the proximal end of the catheter include a stopcock 111 that communicates with the distal (floating-aid) balloon lumen B, and a first hub or extension port 112 that communicates with the distal-aperture lumen D. The stopcock 111 is thus for use in inflating (or deflating) the distal balloon 104. The port 112 is for use in measuring pulmonary-artery pressures or injecting medication into that artery—or, on a drip basis, both simultaneously.

In addition, the termination devices 107 include an electrical connector 114, which provides connection points for the thermistor leads T. A threaded section 146 is advantageously provided at the proximal side of the connector cap 145 to securely engage a mating connector of the previously mentioned control-and-readout electronics module 221 that provides excitation and interpretation for the thermistor T'.

Also among the termination devices 107 are two other hubs 115 and 116. Of these, one port 116 communicates with the proximal lumen P as previously noted, for injection of a cold bolus into the heat-exchange balloon 201 for cardiac-capacity tests as already described.

The other port 115 connects with the pacing-and-medication lumen P/M to guide the coaxial pacing wire 139 (and drip medication) to the right ventricle. A Touy-Borst connector allows both electrical hookup to the wire and medicine injection. (As preferred, a fluid column in this lumen can be used instead to measure right-atrium or right-ventricle pressure; or to infuse liquid at the port 115, particularly if the optional lumen 202 is omitted.)

The stopcock 111 and the hub or extension ports 112, 115 and 116 all end in respective liquid-transfer fittings 141, 142, 147 and 148—which are adapted for pressurized attachment of hypodermic-style injecting apparatus when desired.

Conventional sealant, potting, cementing and securing compounds generally available on the open market and familiar to cardiovascular-catheter artisans are used throughout our invention—including the points at which the various parts (e.g., the manifold 105, catheter 101/103, and single-lumen tubes 106) are held together. As is well known in this field, all components and materials that are to be exposed to the patient's cardiovascular system must be appropriately inert, amenable to sterilization, and preferably supplied sterilized.

Figure 6:
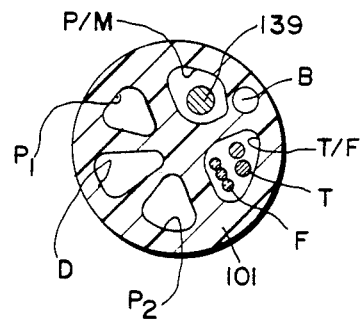
FIG. 6 is a catheter body cross-section, similar to FIG. 2 but showing another preferred form with six lumens.

As shown in FIGS. 6 and 7, another preferred embodiment of our invention has two (rather than only one), lumens $P_1$, $P_2$ for transport of the heat-exchange medium between the heat-exchange balloon 201 and the external heat sink 211. When alternating removal and addition of heat are employed as described earlier, the same two lumens $P_1$, $P_2$ can be used for transport of the heat-exchange medium between the heat-exchange balloon 201 and an external heat source 228.

The source 228 takes the form of heat-exchange coils 228 in a separate section of the same bedside module 211 that houses the Peltier-cooler heat-exchange-medium coils 212. An insulating block 224 separates the hot and cold sections. An electrically actuated flow-diversion valve 225 directs heat-exchange medium from the tube 213 either into the cooled coils 212 or—via a transfer passage 227 —into the heated coils 228.

A return passage 229 from the heated coils 228 joins the outlet line from the cooled coils 212 to the extension tube 203. For better heat isolation a second flow-control valve 226 may be provided at this junction. Electrical power for the control valves 225, 226 and the heater wiring (not shown) as well as the Peltier-cooler wiring (not shown) is supplied through the umbilicus 222.

The exterior of the FIG. 6 and 7 catheter is essentially as shown in FIG. 1, with the exception of an additional extension tube 209 at the proximal end for connection with the return lumen $P_2$. In yet another a variant of the lumen allocations suggested in relation to FIGS. 2 and 6, one of the heat-exchange-medium paths can follow the same lumen T/F occupied by the thermistor leads T (and optic fibers F if present), while the other heat-exchange-medium path follows a separate lumen P (FIG. 2).

The two-lumen arrangement has the advantage that the system can be effectively flushed with the cold (or hot) heat-exchange liquid. Through use of two lumens, a particular slug of heat-exchange medium from the heat source or sink can be advanced positively into the balloon 201 as desired. In this way it is possible to bring the temperature of the input lumen and the balloon more nearly to the temperature of the heat-sink coils 212 (or source coils 228).

As previously indicated, any such technique for raising the temperature differential between the blood and the cold heat-exchange medium improves the signal-to-noise ratio. This measurement strategy is subject to usual medical considerations including patient tolerance of the temperature exposure.

In order to determine more precisely the heat energy extracted from the patient's blood stream, it is desirable to estimate accurately the temperature of the heat-exchange medium within the heat-exchange balloon 201. As already suggested, this can be accomplished with two thermistor beads as follows.

One thermistor bead may be placed in the lumen of the inlet extension tube 203; this bead 401 can then be used to measure the temperature of the fluid flowing into the catheter 101 and ultimately to the balloon 201. Similarly, another thermistor bead 402 may be placed in the lumen of the return extension tube 209, and used to measure the temperature of the fluid leaving the catheter. Insulated wires 403 and 404 electrically connect the thermistor beads 401, 402 to the monitor and computer 221.

The heat flow from the patient may then be precisely and automatically estimated from the temperatures of the heat-exchange medium entering and leaving the catheter, and the mass flow rate established through the catheter. This preciseness aids in computing cardiac output, since the area under the temperature-time curve measured in the pulmonary artery with the thermistor bead located at T/F' is directly proportional to the total thermal energy transferred—as well as inversely proportional to the cardiac output.

The heat-exchange medium is moved through the catheter proximal portion 101 by a pump 231—either a syringe pump or a precision continuous pump. The medium is circulated between the balloon 201 and an external heat sink 212 or source 228 coils.

Provision of two lumens $P_1$, $P_2$ simplifies this operation in that the motor 216, the pump 231, and the heat-exchange medium may always move in the same direction. In this way, medium of a particular specified temperature can be very quickly advanced and positively positioned in the balloon as desired.

To use a periodic heat-removal process, the medium is pumped through the system to adjust the balloon temperature on a timed periodic basis—preferably every two to five minutes. The thermistor signal or signals (as suggested above, the number of thermistors may be one, two or three) pass into an analog-to-digital converter (not shown) within the readout-and-control unit 221, and are digitized. If two or three thermistors are in use, their signals may be multiplexed into a single converter.

A computer (not shown) in the same unit 221 analyzes the data and computes a cardiac output value from the digitized signal—dividing an empirical proportionality constant by the calculated area under the temperature-vs.-time curve. As an example, for a five-cubic-centimeter bolus into a balloon having a seven-cubic-centimeter capacity, the proportionality constant appears to fall into the range of 1.5 to 2.2 liters per minute per degree-Celsius-second (or 25 to 37 milliliters per second squared per degree Celsius).

As stated earlier, this proportionality constant can be more precisely estimated with the information derived from external thermistors 403 and 404, or from an auxiliary thermistor in the heat-exchange balloon, as well as the flow rate and duration of an injection of the heat-transfer medium, and other parameters—including the heat capacity and density of the medium. More specifically, for a constant flow rate, the proportionality constant is itself proportional to (1) the difference between the time-averaged temperatures measured by the return and inlet temperature sensors 402 and 401 and (2) the flow rate of the fluid heat-transfer medium.

If a steady-state method is to be used as mentioned earlier, the initial temperature of the pulmonary artery blood should be estimated before starting the heat-transfer process. This estimate may be made by averaging temperature for five to fifteen seconds or by estimating baseline temperature trends.

Next a pump is activated to maintain a flow of cold saline to the catheter heat exchanger 201 for a fixed period of time in the range of fifteen to forty seconds. During the cold-saline flow, a temperature decrease should be measured in the pulmonary artery.

Cold-saline flow is then stopped, and the catheter and pulmonary-artery blood return to baseline temperature. A new baseline temperature is next estimated. By interpolating between the initial and final baseline temperatures, the decrease in temperature due to the cooling process can be more accurately estimated even in the presence of thermal noise.

Figure 9:
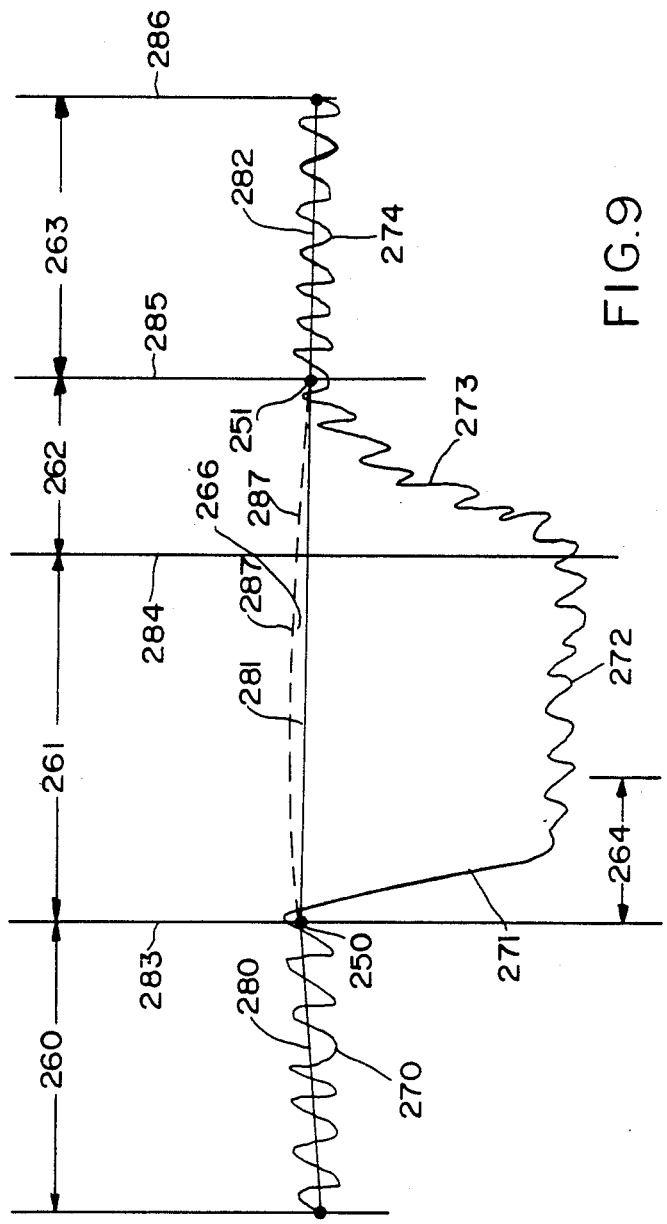
FIG. 9 is a somewhat conceptual diagram representing one typical variation of monitored temperature with time, and a corresponding schema for data handling, particularly related to the steady-state form of the method of our invention.

FIG. 9 represents a time-temperature relation before, during and after a steady-state cold infusion. A straight baseline 280 is fitted through the temperature curve 270 during the preinfusion baseline time 260. This baseline time 260 may last for fifteen to thirty seconds.

The temperature represented by the fitted baseline 280 at the moment 283 when the cold-saline flow is initiated can be used as an estimate of starting baseline temperature. Point 250 represents this value.

After the cold flow is turned off, the system returns to baseline behavior as the cooled blood washes out of the right ventricle and the heat exchanger warms up—along the line 273. The length of time 262 required to complete this temperature recovery can be derived from empirical heat-exchanger warm-up rates and from the length of the temperature-decay interval 264 at the onset of cooling.

In this way a suitable moment 285 is selected as the nominal end of the recovery function 273. That time 285 in turn establishes the start of the postinfusion baseline time 263. The end 286 of the postinfusion baseline time 263 occurs fifteen to thirty seconds later.

Fitting another straight baseline 282 through the temperature data 274 during the postinfusion baseline time 263 establishes a point 251 occurring at the onset of the postinfusion baseline time. The temperature value represented by that point 251 is the averaged temperature value for that instant 285.

Interpolating a straight line 281 between the starting and ending baseline temperature values 250 and 251 establishes a moderately accurate temperature baseline 281 during the cold-flow process. Once a baseline (such as 281) is established, cardiac output can be calculated on a generally continuous basis, using a suitable mathematical relation between cardiac output and the monitored temperature as a function of time.

One such mathematical relation is an adaptation of the inverse proportion between cardiac output and "area under the curve." This proportion was mentioned earlier in connection with prior-art cold-bolus injection methods. Accordingly, the cross-hatched area 265 is inversely proportional to an accurate value of cardiac output, for a fixed cold-flow time 261 (ending at the instant 284 when the pump is shut off) and fixed rate of heat delivery from the heat exchanger.

Accuracy can be slightly improved, however, when as shown in FIG. 9 the preinfusion and postinfusion baselines 280, 282 are not colinear. This improvement is obtained by interpolating a baseline 287 that is instead curved—and by accordingly including within the area of interest the additional segment 266.

In the case illustrated, the curved interpolation baseline 287 and accordingly the curved segmental area 266 are convex upward. As will be clear, in other instances the curved interpolation baseline 287 may equally well be concave upward, making the segment 266 negative; or under rapidly changing conditions may be a compound curve defining a net correction area 266 that is either positive or negative.

In purest principle this method can be extended on a substantially continuous basis by recalculating the total area under (or, as drawn in FIG. 9, above) the curve 271, 272 numerous times while the pump continues to operate. Such continuous extension is limited, however, by the unavailability of fresh baseline data while the pump operates.

Yet another algorithm can be used for rectangular-wave excitation—that is, for alternation between flows of cold fluid and warm fluid in the heat exchanger, or substituting no flow for warm fluid flow. In such situations cardiac output is inversely proportional to the amplitude of the fundamental frequency component measured in the pulmonary-artery blood temperature.

This method appears to offer the advantage that noise due to low-frequency drift may be filtered out with a bandpass filter centered about the fundamental frequency of the excitation. This approach was discussed in considerable detail, though in another context (periodic resistive heating only) by Philip et al., in their previously mentioned paper.

The steady-state method has some advantages, particularly that it can be used with smaller balloons or less efficient heat-exchange methods than the transient method. This is primarily because a large gradient may be maintained for a relatively long time (fifteen to fifty seconds).

Alternatively, in a slightly different form of steady-state technique, the pump can be servocontrolled on a continuous but slowly varying basis to hold the monitored temperature very nearly constant. The amount of heat removed in this way—and therefore the blood flow rate—can be calculated continuously from the servomechanism operating profile. This system too is less precise and accurate than the optimum periodic method.

We believe that the best signal-to-noise ratio is obtained by exchanging heat with the bloodstream in a narrowly defined region, as well as in narrowly defined time intervals. This requirement, however, is not absolute.

If preferred, heat can be removed from (and added to) the bloodstream over a considerable part of the catheter length—such as, for example, the most distal twenty centimeters. This configuration tends to diffuse the thermodilution effect in a geometric way, and thereby to degrade the signal-to-noise ratio.

It does, however, have the important advantage that a relatively large heat-exchange area can be provided without the necessity for a balloon that is relatively large in the transverse direction. In other words, this approach permits use of a catheter having a normal slender diameter along its entire length.

FIG. 8 shows in cross-section a catheter with this sort of longitudinally extended heat-exchange section. As illustrated, the heat-exchange device here can be provided by forming the most proximal segment of the exchange-medium lumens $P_1$, $P_2$ with very thin walls $W_1$ and $W_2$.

If desired, an insulating lumen I can be provided between the inlet lumen $P_1'$ and outlet lumen $P_2'$ to serve as heat-transfer inhibiting means. For best insulation, this lumen I may be partially evacuated in use; or at manufacture may be filled with a polymeric material that cures to form a foam-like filler.

In principle its opposing faces S can be separately metalized to provide specularly reflecting surfaces at both sides of the partial vacuum or foam filler, for even better insulation. As will be apparent, however, such an effort may not be economic.

Such a catheter may be easier to insert through the patient's veins and atrium, particularly for children and other small patients. It may be preferred for many veterinary applications.

It will be understood that the foregoing disclosure is intended to be merely exemplary, and not to limit the scope of the invention—which is to be determined by reference to the appended claims.

We claim:

1. A process for determining flow rate of blood along a flow path in a living body, comprising the steps of:
    a. removing heat from such blood flowing through such body, by heat exchange at a position along such flow path, without liquid injection into such blood;
    b. monitoring temperature;
    c. determining flow rate from the monitored temperature and known parameters related to the amount of heat removed;
    d. periodic repetition of steps a–c;
    e. between each pair of successive periodic repetitions, adding heat to such flow of blood; whereby a balance of heat flow to and from such body is at least roughly preserved and temperature modulation of such blood flow is increased.

2. The process of claim 1, wherein:
    heat is removed for a much shorter time than heat is added; and
    the rate of heat removal is much greater than the rate of heat addition.

3. A cardiovascular diagnostic system, for use with a heat-exchange medium in determining flow rate of blood along a flow path in a living body, comprising:
    a catheter having a distal end for insertion into such blood flow path in such body;
    a heat-exchange device positioned along the catheter;
    means for conveying such medium along the catheter, to and from the heat-exchange device, relative to a position outside such body; said conveying means comprising a pair of lumens defined within said catheter;
    insulating means interposed between said lumens for minimizing heat transfer between said pair of lumens;
    means for cooling such medium to a temperature below blood temperature in such body, for use in the heat-exchange device;
    the heat-exchange device and conveying means being adapted to permit withdrawal of heat from such blood into such heat-exchange medium, but to prevent flow of such medium itself into such blood; and
    means, disposed along the catheter, for monitoring temperature.

4. The system of claim 3, wherein:
    the heat-transfer minimizing means comprise, between said two lumens, a barrier lumen which during use is filled with gas at a pressure significantly lower then atmospheric pressure.

5. A cardiovascular diagnostic system, for use with a heat-exchange medium in determining flow rate of blood along a flow path in a living body, comprising:
    a catheter having a distal end for insertion into such blood flow path in such body;
    a heat-exchange device comprising a thin walled, flexible balloon positioned along the exterior of said catheter;
    means for conveying such medium along the catheter, to and from the heat-exchange device, relative to a position outside such body;
    means for cooling such medium to a temperature below blood temperature in such body, for use in the heat-exchange device;
    the heat-exchange device and conveying means being adapted to permit withdrawal of heat from such blood into such heat-exchange medium, but to prevent flow of such medium itself into such blood; and means, disposed along the catheter, for monitoring temperature.

6. The system of claim 5, wherein:
the balloon comprises a thin wall of irradiated polyethylene or of the material available commercially under the name Mylar.

7. The system of claim 6, wherein:
the wall thickness is on the order of 0.05 millimeter (0.002 inch).

8. The system of claim 7, wherein:
the balloon, when in use, has diameter generally in the range three-tenths to two centimeters and length in the range six to ten centimeters.

9. A cardiovascular diagnostic system, for use with a heat-exchange medium in determining flow rate of blood along a flow path in a living body, comprising:
  a catheter for insertion into such body, and having:
    a distal end for insertion into such blood flow path in such body,
    a proximal end for maintenance outside such body,
    a thin walled balloon of high conductivity plastic positioned along the catheter nearer to the distal end than to the proximal end,
    at least one lumen communicating between the interior of the balloon and the proximal end,
    a temperature-measuring element, disposed near the distal end, that has an electrical parameter dependent upon temperature of the element, and
    electrical connections for transmitting a signal dependent upon the electrical parameter to outside such body;
  a heat sink for use outside such body and defining a fluid-flow path that communicates with the proximal end of the catheter;
  a controllable fluid-moving device in communication with the fluid-flow path; and
  an electronic device, for use outside such body and connected with the heat sink and also receiving said electrical connections from the temperature-measuring element, for controlling the heat-sink temperature and also for monitoring the electrical parameter of the element and displaying data derived therefrom.

10. The system of claim 9, wherein
the balloon is of high-silica-loaded plastic.

11. The system of claim 10, wherein:
the temperature element is a thermistor, the parameter is resistance of the thermistor, and the signal is current which is controlled by the thermistor resistance.

12. The system of claim 10, wherein:
the temperature element is a thermocouple, the parameter is voltage from the thermocouple, and the signal is the thermocouple voltage.

13. The system of claim 9, wherein:
the balloon is of high-thermal-conductivity plastic such as high-silica-loaded plastic;
the temperature element is a thermistor, the parameter is resistance of the thermistor, and the signal is current which is controlled by the thermistor resistance;
the heat sink comprises a Peltier cooler connected with the electronic device for control thereby and in thermal communication with the fluid-flow path; and
the fluid-moving device comprises a syringe and a syringe-driving motor connected for automatic control by the electronic device.

* * * * *